US010682107B2

(12) United States Patent
Hjärn et al.

(10) Patent No.: US 10,682,107 B2
(45) Date of Patent: Jun. 16, 2020

(54) METHOD AND ARRANGEMENT RELATING TO X-RAY IMAGING

(75) Inventors: Torbjörn Hjärn, Vaxholm (SE); Magnus Hemmendorff, Årsta (SE)

(73) Assignee: PHILIPS DIGITAL MAMMOGRAPHY SWEDEN AB, Stockholm (SE)

( * ) Notice: Subject to any disclaimer, the term of this patent is extended or adjusted under 35 U.S.C. 154(b) by 1070 days.

(21) Appl. No.: 12/023,304

(22) Filed: Jan. 31, 2008

(65) Prior Publication Data

US 2008/0198966 A1 Aug. 21, 2008

Related U.S. Application Data

(60) Provisional application No. 60/887,598, filed on Jan. 31, 2007.

(51) Int. Cl.
*A61B 6/00* (2006.01)
*A61B 6/02* (2006.01)
*A61B 10/02* (2006.01)
*A61B 90/11* (2016.01)
*A61B 34/10* (2016.01)

(52) U.S. Cl.
CPC ............. *A61B 6/466* (2013.01); *A61B 6/025* (2013.01); *A61B 6/502* (2013.01); *A61B 10/0233* (2013.01); *A61B 34/10* (2016.02); *A61B 90/11* (2016.02)

(58) Field of Classification Search
USPC ........ 378/4, 21; 382/131; 600/407, 410, 425
See application file for complete search history.

(56) References Cited

U.S. PATENT DOCUMENTS

| 5,913,863 A * | 6/1999 | Fischer .............. A61B 17/3403 600/417 |
| 2005/0124845 A1* | 6/2005 | Thomadsen et al. ............. 600/7 |
| 2008/0187095 A1* | 8/2008 | Boone et al. ................... 378/37 |
| 2009/0003519 A1* | 1/2009 | Defreitas et al. ............... 378/37 |
| 2009/0093715 A1* | 4/2009 | Downey et al. .............. 600/437 |

OTHER PUBLICATIONS

Smith, A., "Fundamentals of Breast Tomosynthesis", Aug. 2008, Hologic Inc., www.hologic.com/data/WP-00007_Tomo_08-08.pdf.

* cited by examiner

*Primary Examiner* — Rochelle D Turchen
(74) *Attorney, Agent, or Firm* — Larry Liberchuk

(57) ABSTRACT

Three-dimensional imaging of a breast tissue is achieved by acquiring a series of X-ray projection images from various angles. A three-dimensional image constructed from the projection images by a computer provides information to the operator to select a coordinate point within the breast from which to obtain a biopsy sample. Acquisition of projection images and construction of three-dimensional images is continued during the insertion of the needle into the breast, during positioning the needle towards the coordinate point, during the sampling and after the sampling. The advantages of utilizing tomosynthesis for breast tissue imaging over stereo imaging include better image quality, easier coordinate measurements within a tissue, ease of use of the equipment by the medical personnel, and fewer image artifact problems.

29 Claims, 2 Drawing Sheets

METHOD AND ARRANGEMENT RELATING TO X-RAY IMAGING

TECHNICAL FIELD OF THE INVENTION

The present invention relates to a method and arrangement in X-ray imaging, in particular three-dimensional imaging, and more especially tomosynthesis and biopsy.

BACKGROUND OF THE INVENTION

Tomosynthesis is used to create a three-dimensional image volume of a person's body part, e.g. her breast, or an object, using X-rays. Currently, tomosynthesis breast imaging is available only for research purposes, but an increasing number of market analysts believe it will become more widely used than conventional two-dimensional mammography.

Tomosynthesis is essentially a limited form of Computed Tomography or CT. Normally, several projection images, e.g. 5 or 30, are acquired in a range of different angles, e.g. −10 to +10 degrees. Each projection image is essentially a conventional 2-dimensional digital X-ray image of the examined object. The projection images are then combined using special purpose software for producing a 3-dimensional image volume, which is a 3-dimensional array of voxels, wherein each voxel is essentially a value corresponding to the X-ray attenuation in one point of the real world. The image volume may also be regarded as a stack of layers or slices, wherein each layer or slice is a 2-dimensional image, which can be displayed as normal image. By definition, the layers are oriented essentially orthogonal to the x-ray beams, or in other words such that they are essentially parallel to the projection images. An un-trained viewer may feel that each layer looks like a projection image; despite it is essentially an extraction of structures at a certain depth in the breast. Typically, the thickness of each layer is about 1 to 2 mm, and the pixel size in each layer is 0.05 to 0.2 mm.

Biopsy is a method for extracting tissue from a breast. It is widely used to extract parts of suspected tumors, in particular micro-calcifications. Most commonly, biopsy is performed using stereo-tactic imaging, wherein two 2-dimensional images projection images are acquired from different angle. The operator selects the same target position (most often a microcalc) in both images and a computer determines the three-dimensional coordinates. In most cases, a needle is inserted through a hole in the compression paddle, whereby the breast deformation moves the micro-calcification close to the point of skin penetration. There are also cases where the needle is inserted from directions along the compression paddle, but that implies a longer distance for the needle to travel through the breast.

Speed is important, since biopsy is uncomfortable for the patient, who has her breast compressed and a needle inserted. Most clinics use the same x-ray apparatus for biopsy as for regular mammography examinations, which implies that the patient has to sit on a chair in an upright position during the examination. It happens that patients faint during examination.

SUMMARY OF THE INVENTION

According to the present invention, tomosynthesis has advantages relative to stereo imaging. Tomosynthesis provide better image quality, and future radiologists will be used to tomosynthesis images. Tomosynthesis also avoids trouble when finding corresponding points in two 2-dimensional images, which would otherwise be difficult for clusters of micro-calc or diffuse contours. In the future, many clinics will have only a tomosynthesis apparatus, and that apparatus must be extended to perform biopsy. A typical tomosynthesis apparatus requires less complicated extensions than transforming the apparatus into a stereo apparatus. The reason is that a typical tomosynthesis apparatus is design to obtain many projection images. Each projection image is acquired with a very low dose and thus noisy. Therefore it is not good to pick two projection images and use them for conventional stereo biopsy. The advantage is extra large for multi-slit scanners that are made for acquiring a large number of projection images. Multi-slit scanners are best suitable for tomosynthesis, wherein they perform quick single-exposure acquisition, in contrast to conventional stereo, which requires two separate exposures.

The present invention circumvents the problems about image artifacts, which are caused when the needle is inserted into the image volume.

The needle is inserted in a direction non-parallel (e.g. 45 degrees) to the direction of the x-rays for each projection, and the needle stops a few millimeters before the target position, which contains the tissue to extract. This approach enables image reconstruction without artifacts around the target position.

If the needle points towards the target position, we can be confident that the needle will actually reach the target position if the needle is inserted deeper into the breast, since movements are accurate along the needle direction. Therefore, there is no need to acquire an image when the needle touches the target position.

Preferably, the present invention comprises a patient support 130, a detector unit 150, a needle 210, a compression paddle 140 with a hole for the needle, a needle holder 240, an x-ray source 110, and a computer 230.

In normal operation the workflow is as follows: The breast 170 is compressed between the patient support and the compression paddle 140. A plurality (typically 10-30) of projection images are acquired from the detector unit, during irradiation by the x-ray source. The projection images are views of the breast from slightly different angles. The computer 230 reconstructs a three-dimensional image volume from the projection images, and displays the image volume to the operator. The operator selects what tissue to extract 171, and indicate the position in the displayed image volume. The computer converts the image volume coordinates to coordinates to the needle. A needle actuator inserts the needle into the breast, as in FIG. 1, such that:

the needle points towards the tissue to extract, and
the needle may move close to the tissue to extract, but it shall reach all the way there, and
The needle points in a direction, which is substantially non-parallel to a plane spanned by the direction of the x-rays for the different projection images. Preferably, the orientation is roughly 45 degrees. (The plane can be understood as slice plane in conventional single-slice CT).

Once again, another set of projection images is acquired, and an image volume is reconstructed. This time, the needle is visible in the projection images, and causes artifacts in the reconstructed image volume. The artifacts propagate along the plane, which is spanned by the direction of the x-rays (more commonly known as slice plane in conventional single-slice CT imaging). Thanks to the clever orientation of position of the needle, there are no image artifacts at the tissue to extract. (The key to understanding the present invention is to understand where artifacts disturb the image volume, and how it depends on the orientation and position of the needle.)

The needle position and orientation is measured, (using the projection images rather than the image volume due to said reconstruction artifacts). The computer estimates the expected path 211 if the needle is inserted deeper into the breast. The computer displays the reconstructed image with overlay graphics showing the needle's position and direction, and displayed. The computer assumes that the needle will be pushed straight inwards and displays the predicted point of intersection with each layer in the reconstructed image volume. FIG. 2 illustrates a user interface for displaying one layer at a time and the predicted path of the needle and the intersection of the viewed layer (red circle).

In case the needle does not point towards the tissue to extract, the needle position is adjusted. The procedure is repeated until images indicate that the needle points towards the tissue to extract.

At this point, the computer knows the distance from the needle to the tissue to extract. The computer shall have information about what kind of needle is connected and where on the needle is the opening for tissue extraction. The needle is inserted an additional distance into the breast, such that the needle opening is at the tissue to extract, and the needle extracts the tissue with a method depending on type of needle.

Some examinations may end by a verification that the desired tissue has been extracted. After tissue extraction, the needle is partially withdrawn, and another image is acquired, wherein the operator can see whether or not the desired tissue has been removed. In case of failure, the needle position may be adjusted in order to obtain more tissue. (This is only possible with needles that can obtain multiple samples, e.g. needle.)

SHORT DESCRIPTION OF THE DRAWINGS

DESCRIPTION OF THE EMBODIMENTS

Figure 1:
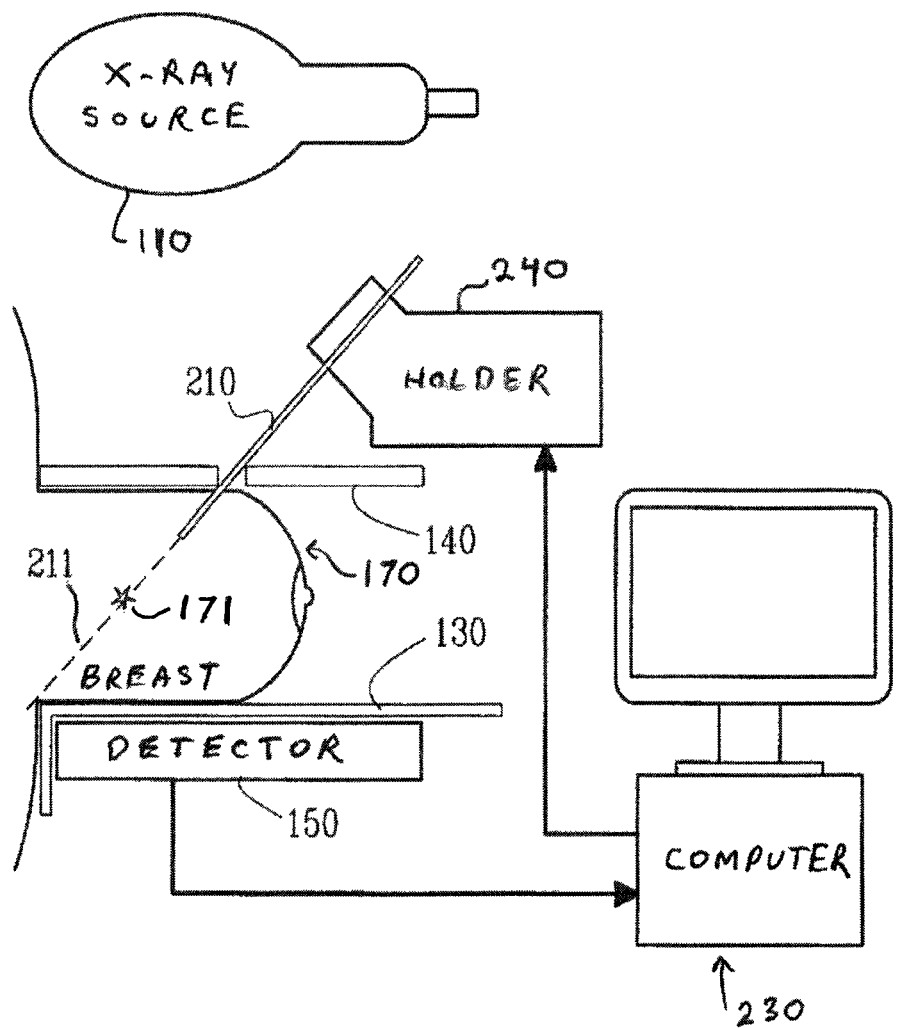
FIG. 1 shows an exemplary embodiment of the present invention, wherein the x-ray source (119) is movable in/out relative the figure plane.
Figure 2:
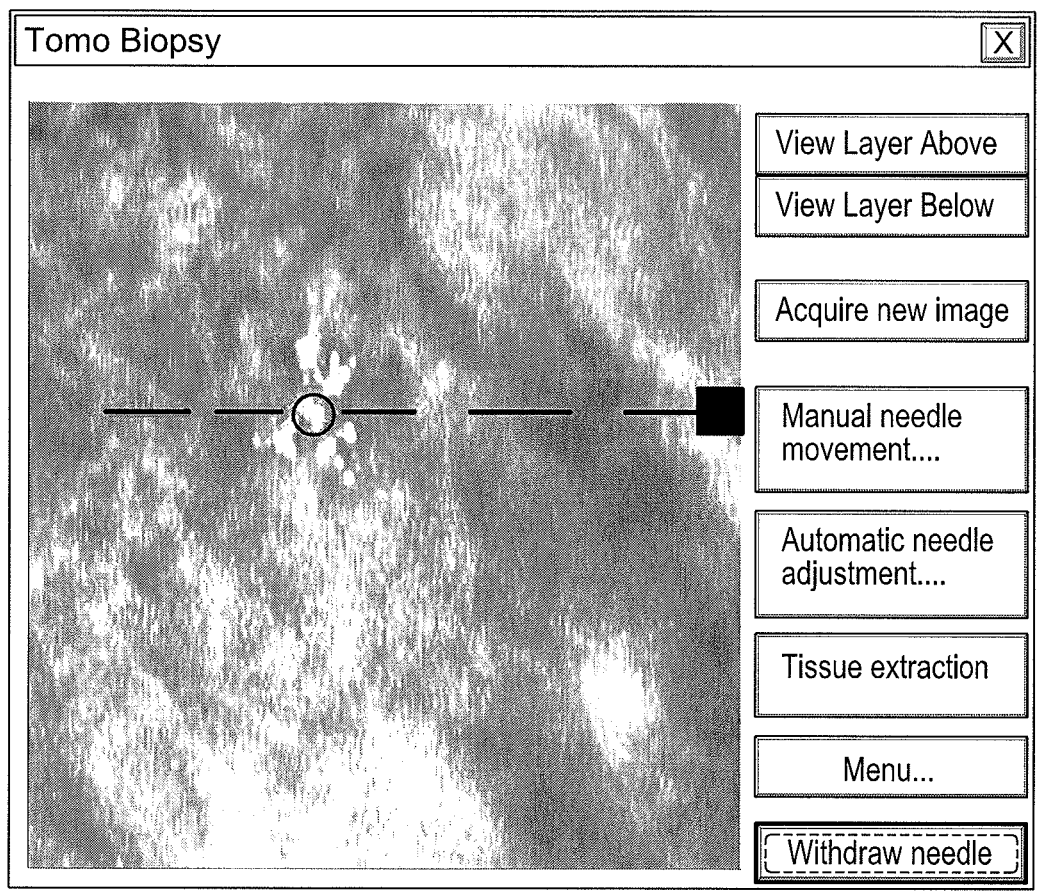
FIG. 2 shows an exemplary computer user interface for displaying predicted point of intersection of the needle in each layer.

The preferred embodiment of the present invention comprises a patient support 130, and a compression paddle 140 for compression of a breast 170 containing a location with some tissue to extract 171. The compression paddle 140 contains a hole for inserting a needle 210 towards said tissue to extract.

Furthermore, the preferred embodiment comprises an acquisition system for obtaining tomosynthesis image data, including a set of projection images (preferably 10-30) and reconstructing a three-dimensional image volume. The acquisition system comprises a detector unit 150, an x-ray source 110, and a computer 230 for reconstruction of a three-dimensional image volume from the set of projection images. The projection images are views of the breast from slightly different angles. The computer 230 reconstructs a three-dimensional image volume from said projection images, and displays the image volume to the operator.

The computer also comprises an algorithm for measuring the needle location and orientation from the projection images. The preferred embodiments avoids measuring the needle position in the image volume, but that requires special care by the image reconstruction algorithm, in order to avoid artifacts, due to dependency of voxel values within a slice, according to well-known prior art of CT image reconstruction.

The preferred algorithm for measurement of the needle position is line fitting to an edge detector, according to prior art. The algorithm may limit the search to an expected region, or perform a full search using the Hough transform or similar.

In the preferred embodiment of the present invention, the computer comprises a user interface for presenting the three-dimensional image volume as a stack of layer images, and there is overlay graphics for presenting the location of the needle, and where it will go if inserted deeper into the breast.

Depending on type of needle and type of examination, the operator may work in different modes. In the first mode, the operator selects a coordinate of the tissue to extract 171, by indicating the position in the displayed image volume. The computer converts the image volume coordinates to coordinates to the needle. In a second mode, the operator does not tell the computer of what to extract. Instead the computer tells the operator the location of the needle, and where it will go if inserted deeper.

The needle will cause image artifacts in the reconstructed image volume. The artifacts spread primarily along the direction of the x-rays and also in the principal plane containing the direction of the set of x-rays through a point.

The preferred embodiment comprises a set of ways for circumventing the problems. Primarily, the needle is inserted substantially non-parallel to said principal plane. The principal plane around the tissue to extract does not contain image artifacts when the needle does not intersect the principal plane containing the tissue to extract.

The preferred embodiment also comprises a function to handle situations when the needle intersect said principal plane. In that case, depending on needle thickness, the image reconstruction either masks the needle prior to reconstruction or of the three-dimensional image volume, or the user interface displays a previously acquired image volume, under assumption that the breast has not moved.

The preferred embodiment comprises a set of these methods depending on needle thickness, location of the opening of the needle (e.g. side or head), amount of tissue to extract, desired accuracy. Some needles are made for hand control, other are suitable for being control by a motor or a hand-driven mechanics. Some needle shall pass the point of tissue to extract. Other extract tissue in the front tip. The preferred embodiment comprises configuration ability for essentially each type of supported needle.

The present invention also comprises a means for constraining the movement of the needle. In particular, the needle shall not penetrate tissue around the ribs of the patient. The preferred embodiment comprises a combination of mechanical stoppers for and software blockers for limiting the amount of needle insertion. The maximum allowed relative movement of a needle is computed using the measurements of the needle position.

The above mentioned and described embodiments are only given as examples and should not be limiting to the present invention. Other solutions, uses, objectives, and functions within the scope of the invention as claimed in the below described patent claims should be apparent for the person skilled in the art.

What we claim is:

1. An apparatus for extracting a body tissue from a body part of a patient, comprising:
   a compression paddle arrangement having a compression paddle and configured for moving said paddle in compressing said body part into a compressed state;
   an acquisition system configured for forming, from said body part in said compressed state, projection images having respective projection directions, through a point in said body part in said compressed state, the projection images being coplanar but angularly different from each other;
   a needle holder configured for holding a medical needle disposed non-parallel to the plane defined by said directions and pointed toward a target point within said body part in said compressed state; and
   a circuit configured for advancing said medical needle into position for an extraction at said target point through said paddle and said body part in said compressed state, with said medical needle in the non-parallel disposition,
   wherein said circuit is further configured to stop said needle a few millimeters before said target point so that an image is reconstructed at said target point without artifacts caused by said needle.

2. The apparatus of claim 1, said body part being a human breast.

3. The apparatus of claim 1, further comprising needle biopsy circuitry configured for, based on user input indicating a location of said target point in an image volume reconstructed from said projection images and responsive to actuation of said advancing into position, controlling, automatically, without need for user intervention, said advancing into position.

4. An apparatus for extracting a body tissue from a body part of a patient, comprising:
   a compression paddle arrangement configured for compressing said body part, said arrangement comprising a patient support configured and arranged for providing underlying support for the compressed body part while an upper-body posture of said patient is upright;
   an acquisition system configured for forming projection images having respective projection directions, through a point in said compressed body part, the projection images being coplanar but angularly different from each other;
   a needle holder configured for using a medical needle for the extracting at a target point within said compressed body part; and
   a circuit configured for advancing said medical needle through said compressed body part, with said medical needle disposed non-parallel to the plane defined by said directions,
   wherein said circuit is further configured to stop said needle a few millimeters before said target point so that an image is reconstructed at said target point without artifacts caused by said needle.

5. The apparatus of claim 1, said medical needle pointing in a needle direction, said advancing into position occurring in said needle direction.

6. An apparatus for extracting a body tissue from a body part of a patient, comprising:
   a compression paddle arrangement configured for compressing said body part;
   an acquisition system configured for forming projection images having respective projection directions, through a point in the compressed body part, the projection images being coplanar but angularly different from each other;
   a needle holder configured for using a medical needle for the extracting at a target point within said compressed body part; and
   a circuit configured for performing, from said projection images, a tomosynthesis based reconstruction of a three-dimensional image volume and for, with said medical needle disposed non-parallel to the plane defined by said directions, advancing, via said needle holder, said medical needle through said compressed body part,
   wherein said circuit is further configured to stop said needle a few millimeters before said target point so that an image is reconstructed at said target point without artifacts caused by said needle.

7. The apparatus of claim 1, further comprising needle biopsy circuitry configured for, after actuation of said advancing into position, causing, automatically, without need for user intervention, both said advancing into position and stopping of said advancing into position at a stopping point a predetermined distance from a predetermined location of said target point.

8. The apparatus of claim 7, said needle biopsy circuitry being further configured for using an image volume reconstructed from said projection images to determine when said stopping of said advancing into position is to occur.

9. The apparatus of claim 8, further configured for deriving said stopping point from user input indicating said location.

10. The apparatus of claim 1, further comprising a display, and needle localization circuitry configured for determining, from said projection images without need of an image volume reconstructed from said projection images, a current position, and current orientation, of said medical needle.

11. The apparatus of claim 10, further configured for, via said display, displaying said volume together with overlay graphics for showing, for said medical needle, a predicted location of where said medical needle will go if inserted deeper into said body part.

12. The apparatus of claim 1, further comprising a user interface, said apparatus being further configured for predicting, based on said projection images, a path of said medical needle into said body part in said compressed state, and for, via said user interface, displaying one layer at a time of an image volume reconstructed from said projection images, said predicted path and an intersection of said path with the viewed layer.

13. A tomosynthesis apparatus having a biopsy function, said apparatus comprising:
   an acquisition system comprising an imaging source and an imaging detector, said system being configured for rotary synchronized motion of said source and said detector to acquire tomosynthesis image data that includes projection images of a body part from different angles, said projection images being in respective, coplanar projection directions;
   a needle holder configured for using a medical needle for extracting tissue at a target point within said body part; and
   a circuit configured for causing said needle holder to advance, through said body part, said medical needle toward said target point, said medical needle being non parallel to the plane spanned by said projection directions, wherein said circuit is further configured to stop said needle a few millimeters before said target point so that an image is reconstructed at said target point without artifacts caused by said needle.

14. The apparatus of claim 13, said processor being further configured for registering said needle holder to imaging derived from said projection images of said body part.

15. The apparatus of claim 14, said processor being further configured for said registering prior to insertion of said medical needle into said body part, for deriving prior to the advancing, from user input, a stopping location of said advancing and for automatically, without need for user intervention, stopping said advancing, enroute to said target point, at said stopping location.

16. The apparatus of claim 13, said body part being a breast, said tomosynthesis apparatus being a breast tomosynthesis apparatus having said biopsy function.

17. The apparatus of claim 13, further comprising a flat compression surface for pressing against and thereby flattening said body part, said projection images being images of said body part flattened by said compression surface.

18. A non-transitory computer readable medium embodying a computer program for tomosynthesis in conjunction with a biopsy function, said program having instructions executable by a processor for performing a plurality of acts, from among said plurality there being the acts of:
acquiring, from an imaging medium, tomosynthesis image data that includes projection images of a body part from different angles, said projection images being in respective, coplanar projection directions;
reconstructing a first three-dimensional image volume from said tomosynthesis data;
automatically causing a needle holder to advance a medical needle, through a body part, toward a target point for extracting at said point a body tissue of said body part, said medical needle being non-parallel to the plane spanned by said projection directions; and
acquiring second tomosynthesis data when the advancing brings the medical needle to a stopping point a few millimeters before said target point so that a second three-dimensional image volume is reconstructed at said target point without artifacts caused by said needle.

19. The apparatus of claim 1, wherein said needle holder is a biopsy needle holder.

20. The apparatus of claim 4, wherein said needle holder is a biopsy needle holder.

21. A method for extracting a body tissue from a body part of a patient, comprising:
compressing said body part vertically;
with said body part compressed, acquiring, from the compressed body part, projection images in respective projection directions, through a point in said compressed body part, that are coplanar but angularly different from each other;
reconstructing a three-dimensional image volume from said projection images;
using a medical needle for the extracting at a target point within said image volume;
inserting, in said compressed body part, said needle such that said needle is disposed non-parallel to the plane defined by said directions and advancing said needle through said compressed body part toward said target point,
wherein said medical needle is configured to stop a few millimeters before said target point so that an image is reconstructed at said target point without artifacts caused by said needle.

22. The method of claim 21, said needle having a tip, said method further comprising:
halting said advancing, before reaching said target point with said tip, to re-invoke said acquiring such that resulting imaging includes said tip; and
re-invoking said reconstructing using said imaging.

23. The method of claim 22, said halting occurring with said needle disposed non-parallel to said plane.

24. The method of claim 22, further comprising, after said halting:
verifying from said resulting imaging, that said needle points toward said target point;
if the needle is verified to be on target, proceeding on to reach, with said tip, said target point and refraining from, upon the reaching of said target point, re-invoking said acquiring; and
if the verifying determines that the needle is not on target, adjusting a position of said needle so as to re-align said needle toward said target point.

25. The apparatus of claim 1, wherein said moving of said paddle moves said paddle vertically.

26. The apparatus of claim 6, wherein said compressing is vertical.

27. The apparatus of claim 13, wherein said plane is vertical.

28. The computer readable medium of claim 18, wherein no x-ray utilized in said acquiring of said second tomosynthesis data that is incident upon said tissue to extract is incident upon said needle as it resides stopped at said stopping point.

29. The method of claim 21,
wherein said acquiring is performed initially, and upon reaching and relative to a stopping point of said advancing;
wherein said stopping point is reached, in said advancing, prior to reaching said target point; and
wherein said method is, provided it is determined, based on the acquisition for said stopping point, that there is no need for trajectory adjustment, without need for any other projection image acquisition as a guide in performing said extraction.

* * * * *